(12) United States Patent
Ray

(10) Patent No.: US 11,801,263 B1
(45) Date of Patent: Oct. 31, 2023

(54) HEARTWORM MEDICAMENT

(71) Applicant: Mike Ray, Canton, MS (US)

(72) Inventor: Mike Ray, Canton, MS (US)

( * ) Notice: Subject to any disclaimer, the term of this patent is extended or adjusted under 35 U.S.C. 154(b) by 0 days.

(21) Appl. No.: 18/115,854

(22) Filed: Mar. 1, 2023

(51) Int. Cl.
*A61K 33/34* (2006.01)
*A23L 27/40* (2016.01)
*A61K 33/32* (2006.01)

(52) U.S. Cl.
CPC .............. *A61K 33/34* (2013.01); *A23L 27/40* (2016.08); *A61K 33/32* (2013.01)

(58) Field of Classification Search
CPC .......... A61K 33/34; A61K 33/32; A23L 27/40
See application file for complete search history.

(56) References Cited

U.S. PATENT DOCUMENTS

| 4,153,547 A | * | 5/1979 | McLean | ................... C02F 5/00 210/749 |
| 2005/0158367 A1 | | 7/2005 | Hershberger | |

OTHER PUBLICATIONS

Drinking Water and Human Health adapted from the 1995 article from Wagenet et al., Home Water Treatment, Aug. 23, 2019). (Year: 2019).*
AJ Karres dated Jan. 23, 2020, "Does Purified Water Have Sodium." (Year: 2020).*
Specification sheet on Acidified Copper Sulfate, Apr. 1, 2018. (Year: 2018).*

* cited by examiner

*Primary Examiner* — Blessing M Fubara
(74) *Attorney, Agent, or Firm* — Dale J. Ream

(57) ABSTRACT

A composition and method for administration to a domesticated animal having heartworm disease includes proportionate amounts of water, acidified copper sulfate, potassium permanganate, and a flavoring agent or binder such as salt.

7 Claims, No Drawings

HEARTWORM MEDICAMENT

BACKGROUND OF THE INVENTION

This invention relates generally to a liquid composition for treating and eliminating heart warms in domesticated animals.

There are a number of conditions and illnesses that can compromise the health and normal activity of animals and, more particularly, of traditional domesticated animals such as dogs. Much like humans visit a doctor when sick, a pet owner is likely to take their canine to a veterinarian when the pet exhibits unusual or degraded activity. Fortunately, the veterinarian may be able to remedy the health issue with a pharmaceutical such as a pill or liquid pharmaceutical.

Unfortunately, there are some medical problems that may affect an animal that are more challenging to treat or that can even be fatal. One such condition is that Pat may have heart warms. Heartworms are literally small worms that are transported by mosquitoes that are infective in household pets such as dogs, cats, and the like. Adult heartworms are able to live in the animal's heart or lungs and may produce offspring. Inside a dog, a heartworm's lifespan is 5 to 7 years. The severity of heartworm disease is related to how many worms are living inside the dog (the worm burden), how long the dog has been infected, and how the dog's body is responding to the presence of the heartworms, An infected canine may exhibit a lack of energy, may have a cough, may even cough up blood, for have a swollen belly due to fluid buildup. If untreated, heartworm disease can be fatal.

Various pharmaceutical compositions have been posed in the art for treating dogs infected with heartworm disease. For instance, heartworm conditions have been treated by using medicaments such as moxidectin, doramectin, moxidectin, selamectin, whether individually or in combination. Unfortunately, traditional treatments can be potentially toxic to a dog and can cause serious life-threatening complications such as blood clots in the dogs lungs. In addition, traditional treatments are very expensive as they require multiple visits to a veterinarian, lab work, and potentially hospitalization and a series of injections.

Therefore, it would be desirable to have a liquid composition that can be readily obtained and mixed by a pet owner and that is effective to eliminate heart warms in a canine. Further, it would be desirable to have a liquid composition that may be administered without one or more injections and as easy as the dog drinking the medicament from his water dish.

SUMMARY OF THE INVENTION

Therefore, a general object of this invention is to provide a liquid composition effective to prevent, treat, and eliminate heart warms in a dog.

Another object of this invention is to provide a liquid composition, as aforesaid, that may be mixed and administered by a pet owner.

Still another object of this invention is to provide a liquid composition, as aforesaid, that is cost effective for the pet owner.

Other objects and advantages of the present invention will become apparent from the following description taken in connection with the accompanying drawings, wherein is set forth by way of illustration and example, embodiments of this invention.

DESCRIPTION OF THE PREFERRED EMBODIMENT

A liquid composition for the prevention and elimination of heartworm's according to a preferred embodiment of the present invention will now be described in detail. The liquid composition includes a mixture of water, acidified copper sulfate, potassium permanganate, and salt.

Preferably, a consumer merely fills a 5-gallon bucket or measures 5 gallons into a larger reservoir and into which specific quantities of the other ingredients may be deposited into the reservoir and stirred until dissolved. Each of the preferred ingredients will be discussed in turn below.

A preferred element of the liquid composition for treating heartworms in dogs is acidified copper sulfate. Acidified copper sulfate is available in 1-pound blocks as a powder and may be diluted by dissolving it in a suitable quantity of water. This substance has been used as a microbial in treating water lines to poultry but may be ingested for suitable treatments as well. Copper sulfate may be acidified so as to reduce its pH and enable more copper to be dissolved into the water which, as a result, makes its use more cost-effective for the consumer.

Another key element of the liquid composition for treating heartworms in dogs is potassium permanganate. Traditionally, potassium permanganate may be sold as a liquid antiseptic solution for external use on a person's skin as it has been shown to have cleansing and astringent effects. It may also be sold in blocks in a powder form. Potassium permanganate is a chemical compound of manganese prepared from manganese dioxide. It is a powerful oxidizing agent. Some amounts of potassium permanganate occur naturally in foods and is considered good for one's health.

Yet another important additive to the liquid composition according to the present invention is salt. Salt, of course, is frequently used in cooking as a flavoring agent. However, salt is also known for its properties as a preservative of chemicals and compositions. Salt further acts as a preservative in that it alters the availability of water in foods so as to impede the growth of pathogens and spoilage organisms when salt is present. Importantly, salt acts as a binder of composition elements and structures proteins to hold the composition together. And, finally, salt contains the element sodium which, in small quantities, is critical to bodily health.

In combination, the elements described above constitute a unique liquid composition that may be safely ingested by canines for the prevention, treatment, or elimination of heartworms. Preferably, the liquid composition is prepared and the following proportions:

5-gallons water
1 lb., Acidified copper sulfate
1 lb., Potassium permanganate
½ lb., Salt In use, it is preferred that the crystal lien or powder materials be added and stirred individually until completely dissolved before the next material is added.

Preferably, the compositions of the present invention are ingested by domesticated animals, preferably, dogs the compositions may be ingested as a supplement to normal dietetic requirements. Stated another way, the compositions of the present invention are intended to be "orally administered" such that a human may be directed to feed or urge the animal to drink the liquid composition described above although, the liquid composition could be administered by a veterinarian using a plunger or by first confining the animal to ensure that a sufficient quantity of the composition is ingested in a short period of time. Depending on factors such as strength of the proportions of the composition, degree of infestation of heartworms in an animal (i.e., the "heartworm burden), risk of repeated infection (i.e., from mosquito bites), the composition may be administered a single time, daily, weekly, or monthly.

It is understood that while certain forms of this invention have been illustrated and described, it is not limited thereto except insofar as such limitations are included in the following claims and allowable functional equivalents thereof.

The invention claimed is:

1. A method for treatment of a canine having heartworm disease, comprising:
   providing a predetermined quantity of water;
   dissolving acidified copper sulfate in said water;
   dissolving potassium permanganate in said water so as to form a composition;
   orally administering said composition to the canine.

2. The method as in claim 1, further comprising dissolving a flavoring agent in said composition.

3. The method as in claim 2, wherein said flavoring agent is salt.

4. The method as in claim 3, wherein said composition is administered daily.

5. The method as in claim 3, wherein said composition is administered weekly.

6. The method as in claim 3, wherein said composition is administered monthly.

7. The method as in claim 3, further comprising proportioning said composition to include:
   5 gallons of said water;
   1 lb. of said acidified copper sulfate;
   1 lb. of said potassium permanganate;
   1/2 lb. of said salt.

* * * * *